United States Patent
Guan et al.

(10) Patent No.: US 11,802,304 B2
(45) Date of Patent: *Oct. 31, 2023

(54) METHOD FOR FRAGMENTING DNA BY NICK TRANSLATION

(71) Applicant: New England Biolabs, Inc., Ipswich, MA (US)

(72) Inventors: Chudi Guan, Wenham, MA (US); Bo Yan, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 246 days.

This patent is subject to a terminal disclaimer.

(21) Appl. No.: 17/243,707

(22) Filed: Apr. 29, 2021

(65) Prior Publication Data

US 2021/0292749 A1    Sep. 23, 2021

Related U.S. Application Data

(63) Continuation of application No. 16/194,552, filed on Nov. 19, 2018, now Pat. No. 11,021,701.
(Continued)

(51) Int. Cl.
*C12Q 1/6806* (2018.01)
*C12N 15/10* (2006.01)
(Continued)

(52) U.S. Cl.
CPC ......... *C12Q 1/6806* (2013.01); *C12N 9/1252* (2013.01); *C12N 9/22* (2013.01);
(Continued)

(58) Field of Classification Search
None
See application file for complete search history.

(56) References Cited

U.S. PATENT DOCUMENTS

| 7,081,358 B2 | 7/2006 | Heiter et al. |
| 7,943,303 B2 | 5/2011 | Xu et al. |

(Continued)

FOREIGN PATENT DOCUMENTS

WO    2018045141 A1    3/2018

OTHER PUBLICATIONS

Chan, et al, Nucleic Acids Research, 2004 32: 6187-6199.
(Continued)

*Primary Examiner* — Samuel C Woolwine
(74) *Attorney, Agent, or Firm* — New England Biolabs, Inc

(57) ABSTRACT

Providing herein, among other things, are kits, compositions and methods that relate to DNA fragmentation. An embodiment of a composition provides combining: one or more enzymes capable of nick translating activity, a dNTP mix comprising at least one dNTP having a modified base, and at least one modification-sensitive nicking endonuclease that is prevented from nicking DNA if its recognition site contains the modified base. When the composition is added to a sample comprising a double-stranded DNA template that comprises recognition sites for the modification-sensitive nicking endonuclease, a reaction mix was produced which could be incubated for any time period in excess of about 5 minutes to produce fragments of a desired size of the double-stranded DNA template. In this method, the fragments produced include the modified base and, as such, are not re-nicked by the nicking endonuclease.

4 Claims, 4 Drawing Sheets

Related U.S. Application Data

(60) Provisional application No. 62/590,087, filed on Nov. 22, 2017.

(51) Int. Cl.
*C12N 9/12* (2006.01)
*C12Q 1/6855* (2018.01)
*C12N 15/66* (2006.01)
*C12N 9/22* (2006.01)

(52) U.S. Cl.
CPC ..... *C12N 15/1065* (2013.01); *C12N 15/1093* (2013.01); *C12N 15/66* (2013.01); *C12Q 1/6855* (2013.01); *C12Y 207/07007* (2013.01)

(56) References Cited

U.S. PATENT DOCUMENTS

| | | |
|---|---|---|
| 2002/0119455 A1 | 8/2002 | Chan |
| 2004/0023207 A1 | 2/2004 | Polansky |
| 2005/0136462 A1 | 6/2005 | Zhu et al. |
| 2007/0161028 A1 | 7/2007 | Schwartz et al. |
| 2008/0268507 A1 | 10/2008 | Xu et al. |
| 2011/0033854 A1 | 2/2011 | Drmanac et al. |
| 2012/0301926 A1 | 11/2012 | Chen et al. |
| 2017/0335371 A1 | 11/2017 | Osborne et al. |

OTHER PUBLICATIONS

New England Biolabs 2015/16 catalog p. 282-287, 297-312.
Sasnauskas, et al, Nucleic Acid Research (2017) vol. 45, 9583-9594.
Margulies, et al., Nature 2005 437: 376-80.
Ronaghi, et al., Analytical Biochemistry, 1996, 242:84-9.
Shendure, Science, 2005 309: 1728-1732.
Imelfort, et al., Brief Bioinform. 2009, 10:609-18.
Fox, et al., Methods Mol Biol. 2009; 553:79-108.
Appleby, et al., Methods Mol Biol. 2009;513:19-39.
Morozova, Genomics, 2008 92:255-64.
Heiter, et al., J. Mol. Biol., 348, 631-640, 2005.

Fragmented *E. coli* gDNA

METHOD FOR FRAGMENTING DNA BY NICK TRANSLATION

CROSS REFERENCE

This application is a continuation of U.S. application Ser. No. 16/194,552 filed Nov. 19, 2018, which claims priority from U.S. Provisional Ser. No. 62/590,087 filed Nov. 22, 2017, herein incorporated by reference.

BACKGROUND

Next-generation sequencing (NGS) relies on the production of high quality sequencing libraries. In many cases, the length of the input DNA should be matched to the NGS platform being used. For example, the read length for the Illumina® (Illumina, San Diego, Calif.) and Ion Torrent Systems® (Life Technologies, Carlsbad, Calif.) are currently under 600 bases, and the read length for the 454 Sequencing® platform (Roche, Basel, Switzerland) is less than 1 kb. As such, in many cases, longer DNA molecules are fragmented to produce shorter DNA molecules prior to library construction. Fragmentation has conventionally been done by physical or enzymatic shearing.

The main physical method used to shear DNA relies on sonication. In these methods, samples are subjected to ultrasonic waves. The ultrasonic vibrations produce acoustic cavitations in the liquid that can shear or break high molecular weight DNA molecules randomly into 100 bp fragments. Sonication shears DNA to produce fragments of the desired size depending on the time and power used. However, sonication methods produce reactive oxygen species that can damage DNA. The production of reactive oxygen species is very sensitive to the reaction condition and it has been found that undamaged DNA can only be produced if particular reaction conditions (e.g., Tris-EDTA buffer and a temperature of about 4° C.) are used. In addition, sonication produces a mixture of blunt ends, 3' overhangs and 5' overhangs, and therefore, end repair is required in order to efficiently ligate the adapters. The end repair step fills in the 5' overhang and removes the 3' overhang, during which a portion of DNA at the 3' overhang is lost.

DNA can also be fragmented enzymatically, e.g., by NEBNext® dsDNA Fragmentase® (New England Biolabs, Ipswich, Mass.). NEBNext dsDNA Fragmentase is a mix of two enzymes: one enzyme randomly generating nicks in the dsDNA and the other enzyme cuts the dsDNA at sites that are opposite to the nicks. The resulting dsDNA fragments contain short overhangs, and thus this method also requires an end repair step in order to efficiently ligate the adaptors to the fragments. Nextera® (Illumina, San Diego, Calif.) tagmentation technology uses a transposase to simultaneously fragment and insert adapters onto dsDNA. These enzymatic methods (i.e. the Fragmentase or tagmentation-based methods) are limited because they are highly sensitive to the ratio of enzyme to DNA in the reaction. If too much DNA or too little enzyme is included in the reaction, then the template is poorly fragmented. If too little DNA or too much enzyme is included in the reaction, then the template is overly fragmented. Moreover, the extent of fragmentation in these enzymatic methods is time-dependent. As such, in order to obtain a desired level of fragmentation, it is important to control the amount of DNA in the sample, the amount of enzyme used, and the time of the incubation. Variation in any of these parameters can cause the DNA fragments to be too long or too short.

NGS technologies have fundamentally changed genomic research and have opened up many new research areas and novel diagnostic applications. Condition-insensitive DNA fragmentation methods may be important for automated library preparation and sequencing, and for the transfer of such technologies into the routine research or diagnostic setting.

SUMMARY

In general, methods and compositions are described for enzymatic DNA fragmentation that can generate fragments of DNA that have a pre-determined size. This method is suitable for a wide concentration range of DNA from picomoles to micrograms.

Various embodiments are exemplified as follows: a method for fragmenting DNA includes forming a reaction mix by combining one or more enzymes that are capable of nick translating activity; a mixture of deoxyribonucleoside triphosphates (dNTPs) that includes at least one modified dNTP, where the modification includes, for example, a change in the base or sugar; and at least one modification-sensitive nicking endonuclease that is prevented from nicking DNA if the recognition site(s) contain the modified base. As such, the nick translated DNA cannot be re-nicked by the at least one nicking endonuclease. Embodiments of the method permit fragmentation, amplification, cloning and/or sequencing of picograms of template DNA. Various embodiments of kits and compositions are also provided that may be used for performing the method.

In general, in one aspect, a kit is provided for fragmenting double-stranded DNA (dsDNA), that includes (i) one or more enzymes capable of nick translating activity; (ii) a dNTP having a modified base; and (iii) at least one modification-sensitive nicking endonuclease that are prevented from nicking DNA if its recognition site contains the modified base.

In examples, the nicking endonuclease in the kit may be Nt.CviPII or NciI or both, the modified base may be a modified dCTP or a modified dATP or both, for example, 5-carboxylcytosine ($^{5ca}C$), 5-methylcytosine ($^{5m}C$), 5-hydroxymethylcytosine ($^{5hm}C$), 5-formylcytosine ($^{5f}C$), 5-bromocytosine, 5-propynylcytosine, 5-iodocytosine, 5-aminoallylcytosine, or 5-propargylaminocytosine, for example the dNTP may be $^{5m}C$. In other examples, the kit contains a dNTP mix, and the modified dNTP is contained in the dNTP mix.

In one embodiment the dNTP corresponds to G, A, T and C, wherein at least one of the dNTPs has a base or sugar that is modified for example the dNTP mix is composed of dGTP, dATP, dTTP and $^{5m}dCTP$ or $^{7m}ATP$ or both $^{5m}dCTP$ and $^{7m}dATP$ or both $^{5m}dCTP$ and dCTP or both $^{7m}ATP$ and dATP or dUTP in place of or in addition to dTTP.

In another example of the kit, the one or more enzymes capable of nick translating activity is provided by a polymerase having a 5'-3' exonuclease activity or a strand-displacing polymerase and a flap endonuclease.

In general, in one aspect, a composition is provided having, one or more enzymes capable of nick translating activity; a dNTP mix comprising a dNTP having a modified base; and at least one modification-sensitive nicking endonuclease that is prevented from nicking DNA if its recognition site contains the modified base.

Examples of embodiments additionally include (a) a dsDNA template for example genomic DNA or an amplicon thereof that comprises recognition sites for the modification-sensitive nicking endonuclease. In other embodiments, the DNA template is fragmented wherein at least some of the fragments comprise the modified base; wherein the fragments may have a desired length selected from a size in the range of 50 bp to 50 kbp.

In general, a method for fragmenting DNA includes:
(a) combining in a reaction mix:
  i. one or more polymerases capable of nick translating activity;
  ii. a dNTP mix comprising at least one dNTP having a modified base;
  iii. at least one modification-sensitive nicking endonuclease that is prevented from nicking DNA if its recognition site contains a modified nucleotide; and
  iv. a sample comprising a dsDNA template that comprises recognition sites for the at least one modification-sensitive nicking endonuclease; and
(b) incubating the reaction mix for a period of time in order to produce fragments of the dsDNA template, wherein the fragments comprise the at least one modified base.

Examples of the method include that the dsDNA template is genomic DNA, or an amplified form thereof, that the template has been fragmented to provide fragments have a desired length selected from a size in the range of 50 bp to 50 kbp, that adaptors are ligated onto the end of the fragments to produce adaptor-ligated fragments, that adaptor-ligated fragments are amplified to produce amplification products, that the fragments are sequenced or used to generate amplification products thereof.

Other implementations, embodiments and advantages may be apparent from the description that follows below.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION

Figure 1:
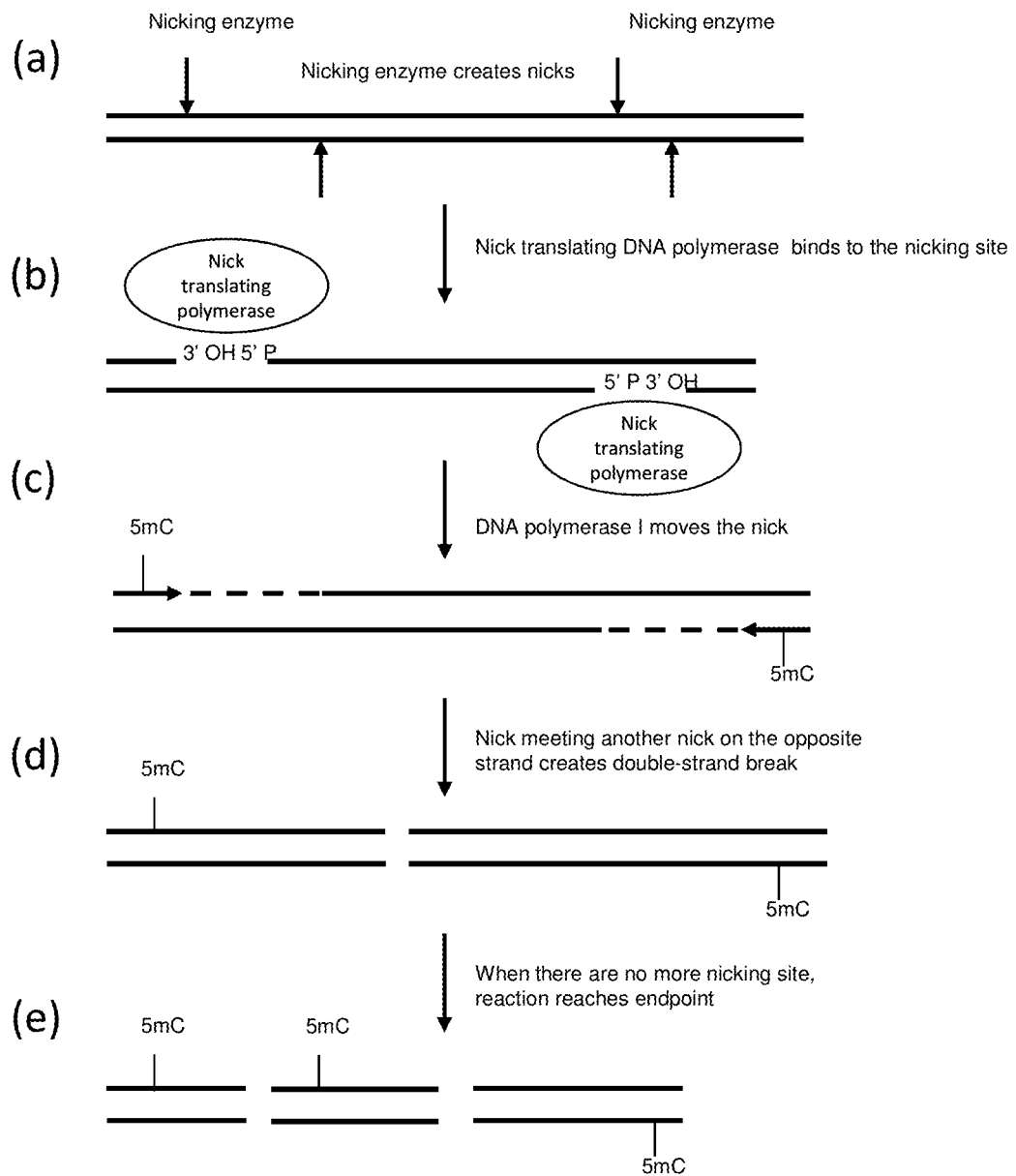
FIG. 1 illustrates some of the principles of the method. (a) and (b) illustrates nicking of template DNA by a nicking endonuclease of choice at site specific sequences. Preferably the nicking endonuclease is a frequent cutter such as Nt.CviPII which recognizes CCD and nicks before the first C. One or more enzyme capable of nick translation (see for example, PolI) binds to the nicking sites to initiate nick translation; (c) the polymerase utilizes the mix of dNTPs including modified dNTPs here illustrated by $^{5m}$C to extend the nicked strand in the direction of the 5'Ps; (d) when a nick occurs on both strands at a single position, a double-strand break results; (e) when there are no new nick sites, the reaction reaches its endpoint.

Unless defined otherwise herein, all technical and scientific terms used herein have the same meaning as commonly understood by one of ordinary skill in the art. Any methods and materials similar or equivalent to those described herein can be used in the practice or testing of the present embodiments although presenting the data for all equivalencies is not practical. Hence representative examples are provided. The teachings of this disclosure are not limited to the particular embodiments described, and can encompass various alternatives, modifications, and equivalents, as will be appreciated by those of skill in the art. The terminology used herein is for the purpose of describing particular embodiments only, and is not intended to be limiting, since the scope of the present teachings will be limited only by the appended claims.

Numeric ranges are inclusive of the numbers defining the range. Each intervening value within the range is to the tenth of the unit of the lower limit to the tenth of the unit of the upper unit unless the context clearly dictates otherwise or other intervening value defined in that stated range.

Nucleic acids are written left to right in 5' to 3' orientation; amino acid sequences are written left to right in amino to carboxy orientation, respectively unless stated otherwise.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All publications, patents, and patent applications mentioned in this specification are herein incorporated by reference to the same extent as if each individual publication, patent, or patent application was specifically and individually indicated to be incorporated by reference. The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Certain terms used herein are described below for the sake of clarity and ease of reference.

The term "non-naturally occurring" refers to a composition that does not exist in nature. In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "plurality" refers to a group that contains at least 2 members. For example, a plurality of labeled nucleotides means 2 or more labeled nucleotides. In certain cases, a plurality may have at least 2, at least 5, at least 10, at least 100, at least 1000, at least 10,000, at least 100,000, at least $10^6$, at least $10^7$, at least $10^8$ or at least $10^9$ or more members.

The term "sequencing" refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" (NGS) refers to the so-called parallel sequencing-by-synthesis or sequencing-by-ligation platforms currently employed by Illumina, Life Technologies, Pacific Biosciences and Roche, etc. NGS methods may also include nanopore sequencing methods or electronic-detection based methods such as Ion Torrent technology commercialized by Life Technologies. "Sequencing" can be performed on any platform known in the art.

The term "extending" refers to the extension of a nucleic acid strand by the addition of one or more nucleotides using a polymerase.

The term "in vitro" refers to a reaction that occurs in a vessel with isolated components, not in live cells. The term "in vivo" refers to cells, tissues or whole organisms that are alive or dead.

The term "reacting" refers to combining under conditions (e.g., a suitable temperature, time and conditions) that result in a reaction, e.g., nicking and/or nick translation, etc.

The term "nick" refers to a site of a broken phosphodiester bond in a nucleic acid that is otherwise double-stranded. A nick contains a 3' hydroxyl and an adjacent 5' phosphate.

As used herein "nicking endonuclease" refers to an endonuclease that cleaves a dsDNA on one strand at or adjacent to a sequence specific recognition site or on two strands sequentially. Some nicking endonucleases exist in nature while others can be engineered from restriction endonucleases.

The term "nick translating" refers to a process in which a polymerase: extends the DNA strand at the 3' hydroxyl at a nick site while, at the same time, the adjacent strand is degraded. In some embodiments, the polymerase itself may have a 5' to 3' exonuclease activity and, as such, the adjacent strand may be degraded by the polymerase. In other embodiments, the polymerase may be strand-displacing polymerase and the adjacent strand may be displaced and degraded by a flap endonuclease (e.g., Fen1).

The term "nick translation activity" refers to either (i) a polymerase that does not displace the strand ahead of it but rather degrades the strand ahead of it using a 5'-3' exonuclease activity or (ii) the combination of a strand-displacing polymerase and a flap endonuclease, in which the polymerase synthesizes and displaces the strand ahead of it and the flap endonuclease then cleaves the displaced strand to leave a nick.

The term "nucleotide" includes dAMP, dCMP, dAMP and dTMP.

The term "nucleoside triphosphates (dNTPs)" include dATP, dTTP, dGTP and dCTP.

Modified nucleotides and modified dNTPs include chemical groups that are covalently linked to the base or to the sugar. Modified bases include methylated purines or pyrimidines, acetylated purines or pyrimidines, alkylated riboses or other heterocycles, hapten or fluorescent labels. Modifications on the sugar moiety which may be ribose or deoxyribose include replacement of one or more of the hydroxyl groups with halogen atoms or aliphatic groups, or are functionalized as ethers, amines, or the like.

The term "dNTP mix" includes the four standard dNTPs—dGTP, dATP, dTTP and dCTP or one or more dNTPs can be partially or completely substituted by one or more modified dNTP. The dNTP mix enables a polymerase to extend by nick translation, a single strand DNA at a nick site, where the newly synthesized nucleic acid contains a mixture of standard nucleotides and modified nucleotides such that the nicking endonuclease can no longer nick the DNA in the newly synthesized DNA. In one example, the dNTP mix contains any one or combination of a modified dGTP, a modified dATP, a modified dTTP, and a modified dCTP along with a complement of standard dNTPs. In one embodiment, a modified dATP or a modified dCTP, or a combination of a modified dATP and a modified dCTP may be used. In some embodiments, the one or more modified dNTPs may replace some or all the corresponding unmodified dNTPs. Preferably dNTPs and modified dNTPs have a 3' hydroxyl so that after they are added to the chain by the polymerase, the polymerase can continue to extend the chain.

The term "modification-sensitive nicking endonuclease" refers to a site specific nicking endonuclease that nicks a dsDNA if the recognition sequence is composed of any or all of guanine, adenosine, thymine and cytosine bases but does not nick if a particular base in its recognition sequence (typically a cytosine) is modified.

Methods of fragmenting DNA for cloning, amplifying and sequencing commonly rely on sonication that produces short fragments of less than 500 bp.

The present method involves combining a polymerase capable of nick translation, a dNTP mix comprising a dNTP having a modified base, a modification-sensitive nicking endonuclease, and a dsDNA template to produce a reaction mix and then incubating the reaction for a period of time of at least 3, 5, or 10 minutes in order to produce fragments of the dsDNA template where there is no upper limit on the incubation time imposed by the fragmentation reaction as the reaction terminates once fragments are formed (although other environmental factors may limit the upper time frame to about 12 hours). The principal of nick translation in the presence of modified dNTPs with an example where the modified nucleotide is $^mC$ is shown in FIG. 1. In this example, the modification-sensitive nicking endonuclease and the nick-translating polymerase (e.g., E. coli DNA polymerase I, full length Bst polymerase or a strand-displacing polymerase with flap endonuclease (e.g., Fen1)) may be combined in the same reaction as a dsDNA template (e.g., genomic DNA) and a dNTP having a modified base (i.e., the same base that the modification-sensitive nicking endonuclease is sensitive to, e.g., $^{5m}C$). As shown, the modification-sensitive nicking endonuclease produces nicks in the dsDNA template, and the resulting 3' hydroxyls are extended by the nick-translating polymerase. The nick translating activity removes the downstream nucleotides using its 5'-3' exonuclease or flap endonuclease activity and replaces them. As a result, the nick "moves along" the DNA. When the polymerase encounters a nick on the opposite strand of the template, the polymerase stops because its template has effectively run out and a dsDNA blunt ended break in the DNA is generated. Incorporation of the dNTP having the modified base into the newly synthesized strand prevents the newly synthesized strand from being digested by the nick-translating polymerase. As such, the newly synthesized strand is not nicked by the nicking endonuclease again, and the reaction reaches an endpoint. At the endpoint of the reaction, the reaction mix contains short double-stranded fragments that have blunt ends, and the recognition sites for the nicking endonuclease in the fragments contain the modified base (e.g., $^{5m}C$).

Fragment Length

As noted above, the fragment length can be tailored to a desired application by altering the ratio of nicking endonuclease to polymerase in the reaction. For example, the amount of nicking endonuclease with a constant excess amount of polymerase in the reaction mix can provide fragments of a defined size range (e.g., where the target size is selected from 50 bp to at least 50 kb, for example, 100 bp, 500 bp 750 bp, 1 kb, 2 kb, 3 kb etc.) when used in conjunction with genomic DNA (e.g., mammalian genomic DNA) or any other large DNA. In these embodiments, the downstream recognition sites for the nicking endonuclease may be "overwritten" by the polymerase before the nicking endonuclease cleaves those sites. The polymerase can overwrite recognition sites for the nicking endonuclease at sites that have already been nicked as well as sites that are downstream from the nicks. In some embodiments, the nicking endonuclease concentration can create fragments that have a length that is much longer than the length of the predicted distance between the recognition sites for the nicking endonuclease. For example, Nt.CvipII should, in theory, nick at sites that are distanced by tens of bases (e.g., Chan et al, Nucleic Acids Research, 2004 32: 6187-6199), but can be used in combination with excess DNA polymerase (FIG. 4 uses an excess of polymerase (20 U) in a reaction mixture containing 1 ug of DNA) to produce fragments that are up to 50 kb in length (see, e.g., the data shown in FIG. 3 of the present application shows fragments of 3,000 bases). In these embodiments, depending on the concentration of nicking endonuclease, not all of the predicted recognition sites (e.g., less than 80%, less than 60%, less than 40%, less than 20% of the predicted recognition sites) in the dsDNA template are cleaved by the nicking endonuclease.

The ratio of nicking endonuclease to polymerase used in the method may vary greatly depending on the desired length of the fragments. In some embodiments, the nicking endonuclease to polymerase ratio (units:units) may be in the range of 1:50 to 1:5000 (e.g., 1:100 to 1:2000) where a unit of polymerase is the amount of enzyme that will incorporate 10 nmol of dNTP into acid insoluble material in 30 minutes. A unit of nicking endonuclease is the amount of enzyme required to digest 1 μg of pUC19 DNA resulting in a stable pattern of fragments under optimal conditions.

Present embodiments have several advantages over sonication. These advantages are associated with combining nicking endonuclease activity with polymerase activity associated with nick translation using a modified nucleotide. The incorporation of the modified nucleotide into the nick translated DNA blocks further nicking activity and hence preselected fragment sizes can be obtained from the enzymatic fragmentation of large or genomic DNA (see FIG. 1). The fragment size is in the first instance predicated on the amount of nicking endonuclease activity present in the reaction in the presence of excess polymerase.

Some of the advantages of the above approach over conventional methods are described below.

(A) A preferred length of fragments of a sample may be desirable when analyzing particular genomes or genomic regions or when using different sequencing platforms. The final length of fragments that are the product of fragmentation of large DNA (such as genomic DNA) may be selected by varying the amount of nicking endonuclease in the reaction mix with respect to the nick translating enzyme(s). For example, larger fragments are obtained by decreasing the concentration of nicking endonuclease in the reaction mix under conditions where the nick translating enzyme(s) are in excess, or if not in excess, the concentration of nick translating enzyme(s) is predetermined. Shorter fragments are obtained by increasing the concentration of nicking endonuclease in the reaction mix under conditions where the nick translating enzyme(s) are in excess or if not in excess, the concentration of nick translating enzyme(s) is predetermined. It is simpler and therefore preferable to maintain the polymerase in excess and vary the amount of nicking endonuclease to obtain the desired fragment size for a particular DNA.

However, it is possible to vary both nicking endonuclease and polymerase to obtain the desired size of fragments. The number of breakpoints (which, in turn determines the average fragment size) can be tuned to be optimal for a particular genome, genomic region, sequencing platform and/or number of different fragmentation breakpoints required for error-correction, as desired.

If longer or shorter fragments are desired (or, alternatively, if the sample is highly A/T-rich or G/C-rich) then the ratio of nicking endonuclease and polymerase can be adjusted. The choice of nicking endonuclease may depend on the overall GC content of the DNA. For example Nt.CviPII is an engineered restriction endonuclease has a recognition site that contains Gs and Cs so that a DNA that has a rich GC content will provide a greater flexibility regarding fragment size than a DNA rich in AT. Other nicking endonucleases here exemplified by NciI are monomeric restriction endonucleases that nick DNA (CC^SGG) and are blocked by $^{5m}C$ among other things, and still other nicking endonucleases recognize sequences that are rich in A and T (e.g. engineered AgsI which can be transformed into a nicking endonuclease and is blocked by $^{m6}A$). Hence depending on the GC/AT content of the DNA, it may be desirable to use a nicking endonuclease that recognizes GC bases and a nicking endonuclease that recognizes AT bases.

Figure 3:
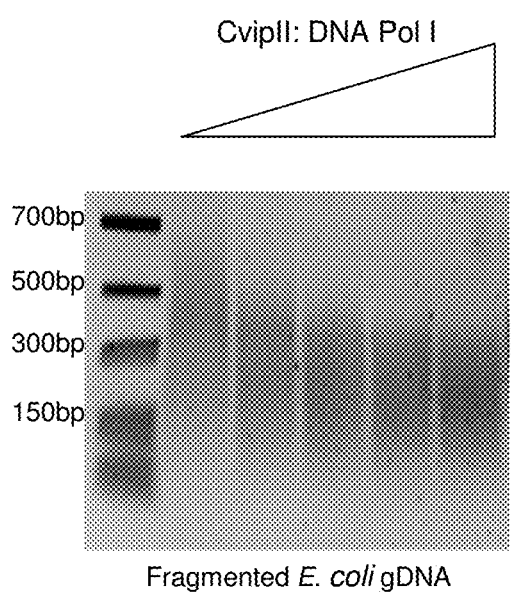
FIG. 3 is a gel showing that fragmentation size can be controlled through regulating the ratio of nicking endonuclease to DNA polymerase I. In this experiment, 0.5 ug E. coli gDNA was fragmented with enzyme mix containing different ratios of nicking endonuclease and DNA polymerase I in the presence of 5-methyl-dCTP for 30 minutes, and 100 ng fragmented DNA was separated on 1.2% agarose gel. The size of fragmented dsDNA increased as the amount of nicking endonuclease decreased. All the five reactions contained an excess of polymerase (here 20 U DNA polI) and from left to right, the reaction contains 0.01 U, 0.02 U, 0.04 U, 0.08 U and 0.16 U CvipII, respective in a 50 ul reaction with 0.5 ug E. coli gDNA and 0.1 mM dNTP (0.025 mM $^{5m}$CTP, 0.025 mM ATP, 0.025 mM GTP and 0.025 mM UP).
Figure 4:
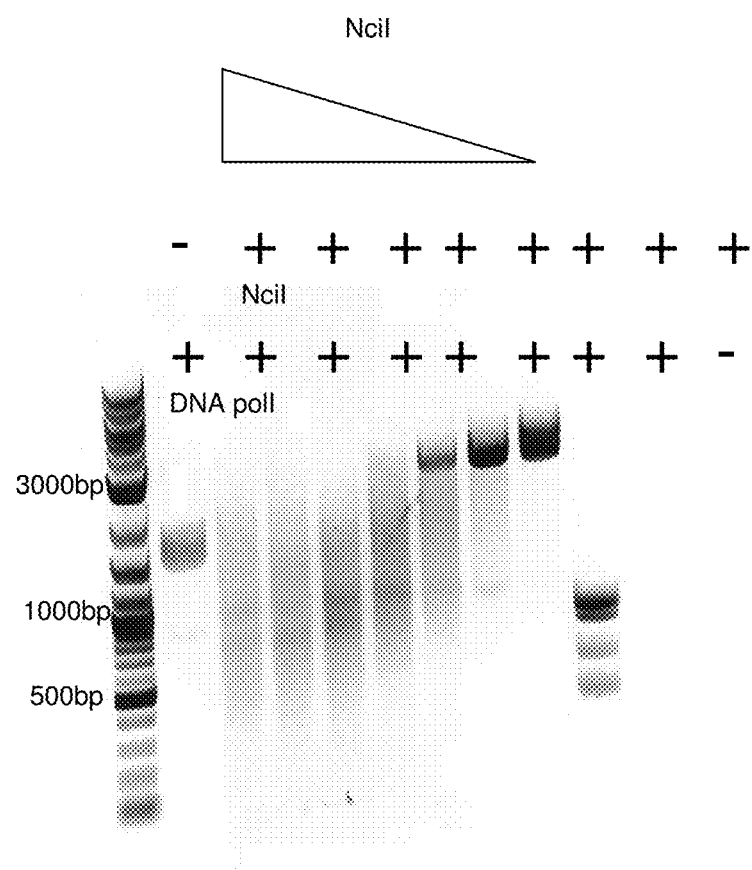
FIG. 4: Homodimer restriction endonuclease NciI restriction endonuclease can also be used to fragment DNA in the presence of DNA polymerase I where reducing the amount of nicking endonuclease results in increased size of fragments. Commercially available restriction endonucleases that are similar to NciI include AsuC2I, BcnI and BpuMI. At least 50 non-commercially available restriction endonucleases similar to NciI have also been identified. In this figure, 1 ug of pUC19 plasmid was fragmented with enzyme mix containing different ratio of restriction endonuclease NciI and DNA polymerase I at room temperature for 1 hour. The DNA polI+reactions have an excess of DNA polymerase (20 U DNA polI) with respect to the nicking endonuclease, while the concentrations of the nicking endonuclease (NciI) in the reaction mix decrease from 20 U, 10 U, 5 U, 2.5 U, 1.25 U, 0.625 U and 0.1325 U (left to right) in a 50 ul reaction with a 0.1 mM dNTP mix including 0.025 mM $^{5m}$CTP, 0.025 mM ATP, 0.025 mM GTP and 0.025 mM TTP.

A suitable ratio of the nicking endonuclease to polymerase can be determined empirically for a DNA as shown in in FIG. 3 and FIG. 4 and used for multiple samples of the DNA.

(B) Blunt ends are formed on the fragments produced by the present method without the need for polishing reactions. Thus "Ligation ready" fragments of a defined size can be produced in a single tube reaction without the addition of new reagents after the reaction has been initiated, without the need for repairing the ends of the fragments after the reaction (although the fragments can be A-tailed if desired), and without the need for specialized, expensive, equipment. Thus, it is believed that the method could be readily automated.

Figure 2:
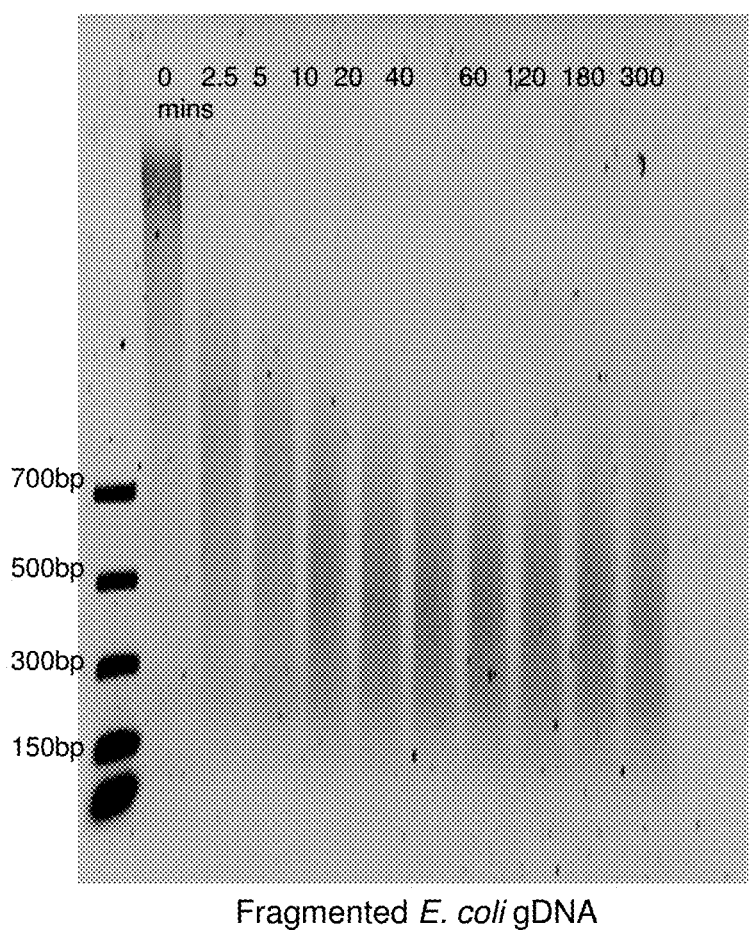
FIG. 2 is a gel showing that the present fragmentation reaction is time independent after reaching its endpoint. In this experiment, 0.5 ug E. coli genomic (g) DNA was fragmented with an enzyme mix containing nicking endonuclease (0.01 U CviPII) and DNA polymerase (DNA PolI 20 U) in the presence of $^{5m}$dCTP for the indicated times, and 100 ng fragmented DNA was separated on 1.2% agarose gel. As shown, after about 20 minutes, the reaction reached endpoint.

(C) The fragmentation reaction is tolerant to an extended incubation time (see for example FIG. 2). Although the fragmentation reaction may be completed within less than 5 minutes or 5-10 minutes, if the experimenter leaves the fragmentation reaction on the bench for as long as 5 hours or as much as 12 hours, no further fragmentation resulting from the nicking endonuclease occurs because the modified nucleotides at the recognition sequences block any further nicking reactions. After about 12 hours at room temperatures, generic environmental factors may cause the DNA to breakdown where these factors are outside the scope of the present methods. In particular, because the length of the fragments is not dependent on the incubation time, several thousand or tens of thousands of samples can potentially be processed en masse in a single run, without the risk that the samples processed at the beginning of the run will be more fragmented than those processed at the end of the run.

(D) Any bias in fragment formation due to the distribution of GC versus AT can be removed by selecting appropriate nicking endonucleases.

(E) In general, the methods and compositions exemplified herein are effective for a wide range of DNA concentrations for example, concentrations of picograms to micrograms of DNA.

Nicking Endonucleases

The nicking endonuclease used in the embodiments should be modification-sensitive in that it does not nick DNA if its recognition site contains a modified base. For example, Nt.CvipII (which is one of the many nicking endonucleases that could be used in the method) is a methylation sensitive nicking endonuclease that recognizes and cuts at the sequences CCD, where D=A, G or T (see, e.g., Chan et al., Nucleic Acids Research, 2004 32: 6187-6199). This sequence is found quite frequently in many genomes. In this example, the dNTP mix can contain 5-methyl-dCTP, and the fragments that are produced by the method may contain $^{5m}C$. Nt.CvipII does not nick at recognition sites that contain $^{5m}C$, and so the fragments are protected from further digestion by this enzyme.

There are many nicking endonucleases now available commercially (see for example the New England Biolabs catalog). Furthermore, it is straightforward to convert a heterodimeric restriction endonuclease into a nicking endonuclease by inactivating one of the two subunits. This has been described in Heiter et al. (U.S. Pat. No. 7,081,358). Other methods of creating nicking endonucleases from restriction endonucleases have also been described (see for example U.S. Pat. No. 7,943,303, US 2005/0136462; US 2008/0268507). Preferably a restriction endonuclease that has a suitable recognition sequence preferably a 3 base or 4 base recognition sequence may be selected that also has a sensitivity to modified bases such that it is blocked from nicking if a modified nucleotide is inserted into the recognition sequence. A sample of restriction endonucleases that are blocked by a methylated C are provided in the New England Biolabs 2015/16 catalog pg. 282-287 with recognition sequences provided on pg. 297-312. Some nicking endonucleases occur naturally such as BstNBI which is a dimer which becomes a monomer on purification because of the weak association of the two subunits. Other restriction endonucleases are monomers that recognize and nick one strand and then move to the second strand to form a nick there too (see for example UbaLAI (Sasnauskas et al, Nucleic Acid Research (2017) vol. 45, 9583-9594). Because these enzymes nick sequentially, the one or more nick translating enzymes can initiate nick translation with modified nucleotides on one strand thereby blocking the monomer from nicking the second strand.

Modified Nucleotides

Base modifications to which modification sensitive nicking endonucleases are sensitive include nucleoside triphosphates that contain methylated purines or pyrimidines, acetylated purines or pyrimidines, alkylated riboses or other heterocycles such as $^{5m}C$ $^{5hm}C$, $^{5f}C$, $^{5ca}C$, 5-bromocytosine, 5-propynylcytosine, 5-iodocytosine, 5-aminoallylcytosine, or 5-propargylaminocytosine, N6-methyladenine, N4-methylcytosine, 8-Oxo-2'-deoxyadenosine (8-oxo-dA), 8-Oxo-2'-deoxyguanosine (8-oxo-dG), O6-methylguanine (O6-m-dG), 1-methyladenine (1-m-dA), O4-methylthymine (O4-m-dT) and β-D-glucosyl-hydroxymethyluracil (Base J) as well as 6 modified adenosine (e.g., N6-methyladenosine and analogs thereof).

In any embodiment, the modified base may contain an affinity tag (e.g., an azide/alkyne group, which is suitable for conjugation to another moiety, e.g., a solid support via click chemistry, or a biotin group so that the labeled nucleic acid can be enriched on a suitable support) or an optically-detectable label (e.g., a fluorophore). The dNTP mix used in embodiments may vary. For example, the dNTP mix used may comprise any one or combination of a modified dGTP, a modified dATP, a modified dTTP, and a modified dCTP.

Enzymes Capable of Nick Translation

Table 1 lists examples of: (i) nick translating polymerases that have a 5'-3' exonuclease activity (for example DNA Polymerase I and the Bst DNA polymerase, full length) and (ii) strand displacing polymerases that can provide a nick translating activity when they are combined with a flap endonuclease such as Fen1 (such as Bst large fragment).

The dsDNA template used in the method may have a median fragment length of at least 1 kb (e.g., at least 2 kb, at least 5 kb, at least 10 kb, or at least 50 kb) and may be at any concentration (e.g., in the range of 5 pg to 1 ug in a 50 µl reaction) and may be from any suitable source. In particular embodiments, the dsDNA template may comprise genomic DNA from a eukaryote, e.g., human, monkey, rat, fish, insect or plant, etc., particularly a mammal, or from a microbe, e.g., virus, archaea, mycoplasma, or a bacterium. The concentration of the dsDNA template may vary greatly and need not be known before starting the method. In some embodiments, the dsDNA template may comprise genomic DNA that has not been amplified. In other embodiments, the dsDNA template may comprise amplified genomic DNA (e.g., genomic DNA that has been amplified by a WGA method) or PCR amplification products.

Source of DNA for Fragmentation

In certain embodiments, the DNA may be obtained from a single cell or a culture of cells, e.g., a cell line. In other cases, the cells may be isolated from an individual (e.g., a patient). The cell or cells may be isolated from a soft tissue or from a bodily fluid, or from a cell culture that is grown in vitro. In particular embodiments, the nuclei may be isolated from a soft tissue such as brain, adrenal gland, skin, lung, spleen, kidney, liver, spleen, lymph node, bone marrow, bladder, stomach, small intestine, large intestine or muscle, etc. Bodily fluids include blood, plasma, saliva, mucous, phlegm, cerebral spinal fluid, pleural fluid, tears, lacteal duct fluid, lymph, sputum, cerebrospinal fluid, synovial fluid, urine, amniotic fluid, and semen, etc. In some embodiments, the chromatin may be from a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In other embodiments, the DNA may be obtained from a microbiome sample, or a bacterial, viral, archaeal or mycoplasma isolate from the environment, cell culture or infected cells.

Fragmentation and Amplification

Because the fragments made by this method have blunt ends, the fragments can be directly ligated to blunt-ended adaptors and then amplified to produce amplification products. The fragments, or their amplification products, can then be sequenced. In some cases, the ends of the fragments could be polished by, e.g., T4 DNA polymerase before ligation to adaptors, but this is unnecessary because the fragments are already blunt ended. In some embodiments, the fragments may be A-tailed by incubation with Taq polymerase and then ligated to T-tailed adaptors. These embodiments can be implemented by adding Taq polymerase to the reaction after it has completed, and then raising the temperature to a temperature of at least 60° C. In some embodiments, the Taq polymerase can be added to the reaction mix prior to incubation. In these embodiments, the fragments can be created at a temperature suitable for nick translation (e.g., a temperature in the range of 20° C. to 42° C., if DNA polymerase I is used), and the fragments produced by the nick translation reaction can be A-tailed by increasing the temperature of the reaction to a temperature suitable for the Taq polymerase (e.g., a temperature of at least 60° C.). In this method, A-tailed fragments can be produced from dsDNA template by (a) combining a nick translating polymerase, a dNTP mix comprising a dNTP having a modified base, a modification-sensitive nicking endonuclease that is prevented from nicking DNA if its recognition site contains the modified base, a sample comprising a dsDNA template that comprises recognition sites for the modification-sensitive nicking endonuclease and Taq polymerase, to produce a reaction mix, (b) maintaining the reaction mix at a temperature suitable for the nick translating activity to produce blunt-ended fragments (e.g., maintaining the reaction mixture at a temperature in the range of 20° C. to 42° C. for at least 10 minutes) and (c) raising the temperature of the reaction mix to a temperature of at least 60° C. for a period of at least 5 minutes to denature the polymerase and permit the Taq polymerase to add a single base overhang to the blunt-ended fragments.

As would be apparent, the adaptor-ligated fragments may be amplified using primers that hybridize to the adaptors, thereby producing amplification products. The primers used to amplify fragments may have a 5' tail that provides compatibility with a particular sequencing platform. Examples of sequencing platforms include those from Oxford Nanopore, Illumina, Pacific Biosystems, Ion Torrent. In certain embodiments, the method may further comprise sequencing amplification products. One or more of the primers used in this step may additionally contain a sample identifier. If the primers use a sample identifier, then products from different samples can be pooled prior to sequencing.

In some embodiments the fragments may be sequenced directly without being amplified. In these embodiments, either the adaptor (or a sequence that is added onto the adaptor by extending the fragment using an oligonucleotide as a template) may have a sequence that is compatible with use in a NGS sequencing platform used.

As would be apparent, the adaptors ligated to the fragments and/or the primers used for amplification may be compatible with use in a NGS platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure (Science 2005 309: 1728); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The fragments may be used on any suitable sequencing platform, including those that are based on sequencing-by-synthesis (i.e., by extending a primer that is hybridized to a template).

Because fragmentation of the dsDNA template is achieved by the action of the nicking endonuclease and the nick translating activity, there is no need to implement other fragmentation methods in the method. As such, in some embodiments, the dsDNA template is not subject to any other fragmentation method (e.g., sonication or the like), that rely on creating nicks by a method other than the nicking enzyme/polymerase method described herein. As such, in any embodiment the dNTP mix may not comprise other modified nucleotides (e.g., dUTP), and the reaction does not include a deglycosylase (e.g., uracil deglycosylase (UDG)) although dUTP may be used in present embodiments to block nicking endonuclease cleavage in the absence of UDG.

Compositions

Also provided are compositions. In some embodiments, the composition may comprise a nick translating activity, a dNTP mix comprising a dNTP having a modified base; and a modification-sensitive nicking endonuclease that is prevented from nicking DNA if its recognition site contains the modified base. The composition may further comprise a dsDNA template that comprises recognition sites for the modification-sensitive nicking endonuclease. In some embodiments, the dsDNA template is genomic DNA (e.g., double-stranded mammalian or bacterial DNA), or an amplified form thereof. In some embodiments, the composition may also contain reaction products, i.e., fragments of the dsDNA template, wherein at least some of the fragments comprise the modified base. The fragments may have a predetermined size for example from 50 bp to 50 kbp. In some embodiments, the composition may additionally comprise Taq polymerase. The potential components of the composition are described in greater detail above.

Kits

Also provided by this disclosure is a kit for practicing the present method, as described above. A subject kit may contain at least: a nick translating activity, a dNTP having a modified base, and a modification-sensitive nicking endonuclease that is prevented from nicking DNA if its recognition site contains the modified base. The details of these components as well as other components that can be optionally included in the kit are described in greater detail above. The dNTP(s) in the stock may be in concentrated form (e.g., a 5× or 10× concentrate) relative to the working concentration described above and, as such, each dNTP may be at a concentration of 500 uM to 50 mM (e.g., 1 mM to 10 mM, or 1.5 mM to 5 mM). The various components of the kit may be present in separate containers, or certain compatible components may be pre-combined into a single container, as desired. In many embodiments, dNTP mix does not comprise other modified nucleotides (e.g., dUTP), and the reaction does not include a deglycosylase (e.g., uracil deglycosylase (UDG)).

In certain cases, the nick translating activity and nicking endonuclease may be precombined in a mixture at a ratio that provides fragments of a particular size (e.g., 150 bp, 200 bp, 300 bp, 400 bp, 500 bp, 600 bp, 700 bp, 800 bp, 900 bp, 1000 bp, etc. up to for example 10,000 kb bp) when used in conjunction with eukaryotic or bacterial genomic DNA. In some cases, the vessel that houses the enzyme mix may be labeled with a size range of expected products.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

TABLE 1

Enzymes that provide a nick translating activity

| I. DNA polymerases with 5'-3' exonuclease activity | II. DNA polymerases with strand displacement activity (requires flap endonuclease, e.g., Fen 1) |
|---|---|
| Family A DNA polymerases | Family A DNA polymerases (requires flap endonuclease, e.g., Fen 1) |
| E. coli DNA polymerase I | Bst DNA polymerase, Large Fragment |
| Taq DNA polymerase | Bsu DNA polymerase, Large Fragment |
| Bsu DNA polymerase, Full Length | Klenow Fragment DNA polymerase |
| Bst DNA polymerase, Full Length | KlenTaq DNA polymerase |
| | Bst 2.0 DNA polymerase |
| | Bst 3.0 DNA polymerase |
| | Bsm DNA polymerase, Large Fragment |
| | Klenow Fragment DNA polymerase, exo- |
| | Hemo Klen Taq |
| | Family B DNA polymerases (requires flap endonuclease, e.g., Fen 1) |
| | phi29 DNA polymerase |
| | Q5 ® DNA polymerase |
| | Vent ® DNA polymerase |
| | Deep Vent DNA polymerase |
| | Phusion ® DNA polymerase |
| | Vent DNA polymerase exo- |
| | Deep Vent DNA polymerase exo- |
| | Pfu DNA polymerase |

All patents and publications, including all sequences disclosed with in such patents and publications, referred to herein are expressly incorporated by reference including U.S. Provisional Application Ser. No. 62/590,087 filed Nov. 22, 2017.

EXAMPLE

Aspects of the present teachings can be further understood in light of the following example, which should not be construed as limiting the scope of the present teachings in any way.

Example 1: Cleavage of Genomic DNA

The following 50 ul reaction mix was produced:
0.5 ug E. coli gDNA
1×NEB buffer 2.1
Nt.CviPII (0.04 U) or NciI (0.1325 U NciI)
E. coli polymerase I (20 U)
dNTP mix (0.1 mM with equal amounts of each component dNTP)

The reaction mix was incubated at room temperature (around 23° C.) for 30 minutes (FIG. 3 and FIG. 4) and 0-300 minutes in FIG. 2.

Fragmentation of E. coli gDNA into double-stranded fragments was completed by 10-20 minutes under conditions that generate a 700 bp fragment (FIG. 2).

The ratio of Nt.CviPII and the polymerase were titrated. The median size of the fragments decreased as the amount of the nicking endonuclease Nt.CviPII (FIG. 3) or NciI (FIG. 4) increased, indicating that the fragment size can be controlled by varying the amount of nicking endonuclease relative to an excess of the polymerase.

The reaction was performed at temperature that varied from 10° C. to as high as 37° C. In all cases, fragmentation ceased when the nick sites contained modified nucleotides.

What is claimed is:

1. A method for generating fragments of DNA of a predetermined size from a genomic DNA, comprising:
   (a) nicking DNA with a modification sensitive nicking endonuclease or homodimer restriction endonuclease and permitting nick translation with a strand displacing DNA polymerase;
   (b) permitting the DNA polymerase to move the nick on one strand of the DNA until the polymerase meets a nick on the second strand;
   (c) preventing secondary nicks at a single site by means of modified nucleotides introduced into the nick site;
   (d) generating fragments having a desired length selected from a size range of 50 bp-50 kb.

2. The method according to claim 1, wherein the homodimer restriction endonuclease is selected from the group consisting of NciI, AsuC21, BcnI and BpuMI and isoschizomers thereof.

3. The method according to claim 1, wherein the nicking endonuclease is Nt.CviPII.

4. The method according to claim 1, wherein (c) comprises selecting a ratio of nicking endonuclease to polymerase in the range of 1:50-1:5000 (units:units).

* * * * *